(12) United States Patent
Nutalapati

(10) Patent No.: US 10,485,770 B2
(45) Date of Patent: Nov. 26, 2019

(54) FUNCTIONALLY-COATED MULTILAYER TABLETS

(75) Inventor: Siva Rama Krishna Nutalapati, Princeton, NJ (US)

(73) Assignee: APTAPHARMA, INC., Pennsauken, NJ (US)

( * ) Notice: Subject to any disclaimer, the term of this patent is extended or adjusted under 35 U.S.C. 154(b) by 1141 days.

(21) Appl. No.: 13/518,038

(22) PCT Filed: Dec. 15, 2010

(86) PCT No.: PCT/US2010/060424
§ 371 (c)(1),
(2), (4) Date: Jun. 21, 2012

(87) PCT Pub. No.: WO2011/078993
PCT Pub. Date: Jun. 30, 2011

(65) Prior Publication Data
US 2012/0258173 A1    Oct. 11, 2012

Related U.S. Application Data

(60) Provisional application No. 61/288,550, filed on Dec. 21, 2009.

(51) Int. Cl.
*A61K 9/24* (2006.01)
*A61K 31/137* (2006.01)

(52) U.S. Cl.
CPC .................................. *A61K 31/137* (2013.01)

(58) Field of Classification Search
CPC ...... A61K 9/20; A61K 9/2004; A61K 9/2072; A61K 9/20086
USPC ................... 424/424–468, 472, 474
See application file for complete search history.

(56) References Cited

U.S. PATENT DOCUMENTS

| | | |
|---|---|---|
| 4,839,177 A | 6/1989 | Colombo et al. ............ 424/482 |
| 5,422,123 A | 6/1995 | Conte et al. ............... 424/479 |
| 5,650,169 A | 7/1997 | Conte et al. ............... 424/472 |
| 5,780,057 A | 7/1998 | Conte et al. ............... 424/468 |
| 6,033,685 A | 3/2000 | Qiu et al. .................. 424/464 |
| 6,294,200 B1 | 9/2001 | Conte et al. ............... 424/472 |
| 6,387,403 B1 * | 5/2002 | Seroff ................ A61K 9/0004 424/464 |
| 6,706,283 B1 | 3/2004 | Appel et al. ............... 424/473 |
| 6,720,005 B1 | 4/2004 | Ayres ........................... 424/480 |
| 6,733,784 B1 | 5/2004 | Ayres ........................... 424/474 |
| 6,770,297 B1 | 8/2004 | Shaw ............................ 424/473 |
| 6,899,896 B2 | 5/2005 | Curatolo et al. ............. 424/473 |
| 7,014,867 B2 * | 3/2006 | Fanara ................ A61K 9/209 424/464 |
| 8,470,367 B2 * | 6/2013 | Bhalachandra Dharmadhikari .... A61K 9/2072 424/464 |
| 2002/0090394 A1 | 7/2002 | Leonard et al. ............. 424/457 |
| 2003/0235616 A1 | 12/2003 | Sowden et al. ............. 424/473 |
| 2008/0003281 A1 * | 1/2008 | Clemmensen ....... A61K 9/1623 424/458 |
| 2008/0095843 A1 * | 4/2008 | Nutalapati ............ A61K 9/209 424/465 |
| 2008/0268046 A1 | 10/2008 | Zuleger et al. ............. 424/472 |
| 2009/0280176 A1 | 11/2009 | Vieira et al. ............... 424/472 |

FOREIGN PATENT DOCUMENTS

WO    WO 2007/149860 A1    12/2007

OTHER PUBLICATIONS

International Preliminary Report on Patentability from PCT/US2010/060424, dated Jul. 5, 2012, PCT.

Abdul, S. and Poddar, S. S. "A Flexible Technology for Modified Release of Drugs: Multi Layered Tablets" Journal of Controlled Release 2004 97:393-405.

Streubel et al. "Bimodal Drug Release Achieved with Multi-layer Matrix Tablets: Transport Mechanisms and Device Design" Journal of Controlled Release 2000 69:455-468.

International Search Report from PCT/US1/60424, dated Dec. 15, 2010, PCT.

\* cited by examiner

*Primary Examiner* — Micah Paul Young
(74) *Attorney, Agent, or Firm* — Licata & Tyrrell P.C.

(57) ABSTRACT

Multilayer functionally coated tablets for oral administration of one or more active pharmaceutical ingredients containing one or more quick release layers and one or more modified release layers separated by an inert layer are provided. Also provided are methods for formulation and use of these tablets.

7 Claims, 1 Drawing Sheet

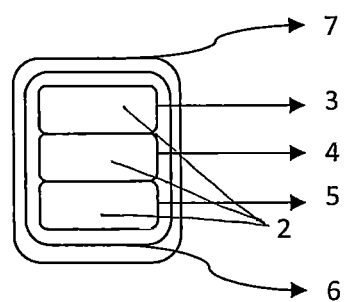

FUNCTIONALLY-COATED MULTILAYER TABLETS

This patent application is the U.S. National Stage Application of International Application No. PCT/US2010/060424 filed Dec. 15, 2010, which claims the benefit of priority from U.S. Provisional Application Ser. No. 61/288,550, filed Dec. 21, 2009, the teachings of each of which are herein incorporated by reference in their entirety.

FIELD OF THE INVENTION

The present invention relates to multilayer functionally coated tablets for oral administration of one or more active pharmaceutical ingredients (API). The multilayer functionally coated tablets contain one or more quick release API containing layers and one or more modified release API containing layers separated by an inert layer. Methods for formulation and use of these tablets are also provided.

BACKGROUND OF THE INVENTION

Various controlled release multilayer tablet are available.

For example, with the Geomatrix™ technology customized levels of controlled release of specific drugs and/or simultaneous release of two different drugs and different rates can be achieved from a single tablet. The controlled release is achieved by constructing a multilayer tablet. The combination of layers, each with different rates of swelling, gelling and erosion, is responsible for the rate of drug release within the body. A disadvantage with this technology, however, lies in partial coating/barrier layer(s) as this results in an area with altering drug release as the matrix erodes. For example, a multilayer tablet can transform to a single matrix exposed on all sides to the gastrointestinal fluids upon detachment of the partial coating/barrier layer. This effect is more pronounced when these tablets are taken with food. In some cases the extent of absorption is 50% lower under fasting conditions when compared to fed conditions.

U.S. Pat. No. 4,839,177 discloses a Geomatrix® system for controlled-rate release of active substances with a deposit core of a defined geometric form comprising a polymeric material having a high degree of swelling and a gellable polymeric material, and a support platform consisting of a polymeric material insoluble in aqueous fluids applied to the deposit core such that it partially coats the deposit core. Although the system provides a uniform rate of release, a disadvantage is that the rigid support platform can crack or flake before the active substance is completely released.

U.S. Pat. Nos. 5,422,123, 5,780,057 and 6,294,200 describe improvements wherein the support platform is made of polymer substances which are slowly soluble and/or gellable in aqueous fluids, and plasticizers, such that the support platform does not crack or flake before the drug is completely released from the deposit core. However, while these patents disclose systems wherein surface area of release is reduced by covering two or more surfaces of the deposit core, in practice such systems are difficult to manufacture at an industrial scale, especially systems wherein two lateral surfaces and one planar surface are coated by the support platform.

Published U.S. Application No. US 2002/0090394 A1 describes a further modified system including a pH-dependent polymer coating, such that the release does not occur in the stomach, but occurs after the system empties from the stomach. However, this system also has disadvantages in that partial coating/barrier layer(s) below the pH-dependent polymer coating cannot be easily applied on a manufacturing scale, if at least three of the four tablet surfaces are to be coated to provide assured zero-order or uniform release. The partial coating/barrier layer(s) may be applied according to published U.S. Application No. only on one surface. This again results in the area not remaining constant if the matrix erodes. It has also been observed that the partial coating/barrier layer can detach itself from the deposit core upon handling and transport.

U.S. Pat. No. 5,650,169 discloses a pharmaceutical tablet capable of releasing the active ingredients contained therein at subsequent times, the tablet being prepared by a process wherein a three-layered tablet core comprising a first drug-containing layer, an intermediate barrier layer and a third drug-containing layer are covered with an impermeable polymeric film. The first layer presents a raised top, which is removed by abrasion so as to allow contact of the abraded first layer surface with the environment. The composition of the barrier layer is designed to modulate release from the third layer of the tablet. A disadvantage of this system is that it requires removal of the raised top layer by abrasion to provide a means for release of the components of the system. This may not be feasible at an industrial scale. Further, if the abrasion is not uniform, the release of the active ingredients will be affected.

U.S. Pat. Nos. 6,720,005 and 6,733,784 disclose coated, platform-generating tablets. The tablet hydrates and expands upon swallowing such that the membrane covering the coating ruptures mostly around the belly-band surface of the tablet due to swelling of the core, thereby exposing the belly surface of the core tablet to hydrating and eroding liquids. A disadvantage of the system is that the coating is not reliably removed from the belly-band surface always but may rupture at a different weak point. Thus, the surface area of exposure may vary. Also, the system shows a lag time of release of half an hour or more. Many shapes of the core have been suggested in the invention but some of these may accentuate the problems encountered during tablet manufacture. Further, the belly-band surface, which is exposed after the coating ruptures, has the least surface area and other more preferred surfaces are not exposed.

U.S. Pat. No. 6,899,896 discloses a controlled release formulation for setraline having a core comprising a setraline containing composition and a water swellable composition, wherein the water swellable composition is in a separate region within the core. The core is coated with a water-permeable, water-soluble coating having at least one delivery port for release of the drug from the core through the delivery port in the coating.

U.S. Pat. No. 6,706,283 also discloses a controlled release formulation for low solubility drugs which is coated with a non-dissolving, non-eroding coating that controls the influx of water to the core to cause extrusion of a portion of the core through one or more delivery ports.

U.S. Pat. No. 6,770,297 discloses a controlled release delivery system for a solid dosage form with a plurality of controls on the release of a drug which may be initiated at different times.

SUMMARY OF THE INVENTION

An aspect of the present invention relates to a functionally coated multilayer tablet comprising a core tablet comprising one or more quick release layers containing an active pharmaceutical ingredient (API) and one or more modified release layers containing the same API or a different API, said core tablet being coated with a functional coating or film.

In one embodiment, the multilayer tablet further comprises an inert layer separating the API containing layers.

In one embodiment, the multilayer tablet further comprises an additional API or APIs in the quick release layer and/or the modified release layer.

Another aspect of the present invention relates to a method for formulating a functionally coated multilayer tablet comprising compressing into a core tablet one or more quick release layers containing an API and one or more modified release layers containing the same API or a different API and coating the core tablet with a functional coating or film.

In one embodiment of this method, the one or more quick release layers containing an API and the one or more modified release layers containing the same API or a different API of the core tablet are separated by an inert layer.

In one embodiment of this method, the method further comprises formulating an additional API or APIs in the quick release and/or the modified release layer.

Another aspect of the present invention relates to a method for orally administering one or more APIs to a subject which comprises administering to the subject a functionally coated multilayer tablet comprising a core tablet comprising one or more quick release layers containing an API and one or more modified release layers containing the same API or a different API, said core tablet being coated with a functional coating or film.

In one embodiment, the functionally coated multilayer tablet further comprises an inert layer separating the API containing layers.

BRIEF DESCRIPTION OF THE FIGURES

FIG. 1 provides a diagram of one embodiment of a functionally coated multilayer tablet of the present invention.

DETAILED DESCRIPTION OF THE INVENTION

The present invention provides functionally coated multilayer tablets for oral administration of an active pharmaceutical ingredient (API) or active pharmaceutical ingredients (APIs). Our system described in here is advantageous in its ability to be easily incorporated into the production line. The core tablets can be manufactured by readily available equipment and the functional coating can be applied by readily available equipment that can be integrated into widely-used pharmaceutical processes, thus giving firms more control over their own production activities. Rather than selecting a particular surface for coating, the present invention allows for coating the whole tablet at the same time providing different drug release profiles from different layers.

Tablets of the present invention comprise a core tablet.

The core tablet comprises one or more quick release API containing layers. By quick release layer or layers as used herein it is meant that part of the core tablet with a dissolution profile relatively faster than the modified release layer. In one embodiment, the dissolution profile of the quick release layer ranges from 0 to 120 minutes in a suitable in vitro dissolution test. A suitable exemplary dissolution test may be, for example, dissolution carried out in 900 mL of phosphate buffer (pH 6.8) at temperature of 37.0° C.±0.5° C. using apparatus II (paddle) rotating at a speed of 100 rpm. However, as will be understood by the skilled artisan upon reading this disclosure, variations on timing range of the quick release in vitro dissolution profile, as well as the dissolution test and apparatus and conditions, well known to those skilled in the art can be used and are encompassed by the present invention. Variations, such as an increase in time of the in vitro dissolution profile of the quick release layer or layers beyond 120 minutes, in no way circumvents the present invention.

The core tablet also comprises one or more modified release API containing layers. In one embodiment, the modified release layer or layers is that part of the tablet with a dissolution profile which is extended, delayed or controlled as compared to the in vitro dissolution of the quick release layer. In one embodiment, the modified release layer has a release profile of 4 hours or greater. However, as will be understood by the skilled artisan upon reading this disclosure, a modified release layer or layers with a release profile shorter than 4 hours can also be incorporated into the core tablet and is encompassed by the present invention. Variations, such as a release profile of the modified release layer or layers of less than 4 hours, in no way circumvents the present invention.

The core tablet may further comprise an inert layer. In one embodiment, the inert layer separates the quick release layer or layers and the modified release layer or layers to minimize the effect of one layer on the other and to control the release of API from the modified release layer(s). In another embodiment, the inert layer may be between quick release layers and/or modified release layers. In one embodiment, by "inert layer" it is meant a layer containing no API or API in an amount which is insignificant to therapeutic activity of the tablet.

The entire core tablet is then coated with a functional coating or film. In one embodiment, the functional coating or film of the tablet of the present invention is porous, thereby permitting quick release of the API from the quick release layer upon oral administration of the tablet. The functional coating or film also works synergistically with the matrix of the modified release layer to control the release of the API from the modified release layer. In one embodiment, the tablet of the present invention is coated with more than one functional coating or film.

In one embodiment, the tablet of the present invention further comprises a subcoating between the core tablet and the functional coating or film.

One embodiment of a multilayer tablet of the present invention is depicted in FIG. 1. In the embodiment depicted in FIG. 1, the core tablet 2 comprises a single quick release API containing layer 3 and a single modified release API containing layer 5, separated by a single inert layer 4. In this embodiment, the core tablet is coated with a subcoating 6 followed by a functional coating or film 7.

As will be understood by the skilled artisan upon reading this disclosure, additional quick release layers and/or modified release layers containing an API and/or additional inert layers can be added to the core tablet and tablets comprising these additional layers are encompassed by the present invention. Addition of such layers in no way circumvents the present invention.

Similarly, additional non-functional and/or functional coatings can be added to the core tablet and tablets comprising these additional coatings are encompassed by the present invention. Addition of such coating layers in no way circumvents the present invention.

Tablets of the present invention can be prepared by methods well-known in the art. Generally recognized compendiums of such methods include Remington: The Science and Practice of Pharmacy, Alfonso R. Gennaro, editor, 20th ed. Lippincott Williams & Wilkins: Philadelphia, Pa., 2000 and Sheth et al. Compressed Tablets, in Pharmaceutical Dosage Forms: Tablets, Vol 1. edited by H. A. Lieberman and L. Lachman, Dekker N.Y. (1980).

Various methods for preparation of quick release layers and the vehicles therein are well-known in the art.

The quick release layer or layers of a tablet of the present invention can be prepared by direct compression of a mixture of the API with a suitable carrier or excipient, such as carbohydrate or protein fillers, such as sugars, including lactose, sucrose, mannitol, or sorbitol; starch from corn, wheat, rice, potato, or other plants; cellulose, such as methyl cellulose, hydroxypropyl cellulose, hydroxypropyl methylcellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; magnesium carbonate; magnesium oxide; and other agents such as acacia and alginic acid.

Agents that facilitate disintegration and/or solubilization are also added, such as, but not limited to, cross-linked polyvinyl pyrrolidone, sodium starch glycolate, Croscarmellose Sodium, alginic acid, or a salt thereof, such as sodium alginate, microcrystalline cellulose and corn starch.

Tablet binders that can be used include acacia, methylcellulose, sodium carboxymethylcellulose, polyvinylpyrrolidone (povidone), hydroxypropyl cellulose, hydroxypropyl methylcellulose, sucrose, starch and ethylcellulose.

Lubricants that can be used include magnesium stearates, stearic acid, sodium Stearyl fumerate, talc, waxes, oils, silicon dioxide and colloidal silica.

Fillers, agents that facilitate disintegration and/or solubilization, tablet binders and lubricants, including the aforementioned, can be used singly or in combination.

The quick release layer or layers of the tablets are then formulated, for example, by preparing a powder mixture by dry blending or granulating or slugging, adding a disintegrant and lubricant and pressing into a tablet layer or layers.

Various methods for preparation of modified release layers and the vehicles therein are well-known in the art. Generally recognized compendiums of such methods and ingredients include Remington: The Science and Practice of Pharmacy, Alfonso R. Gennaro, editor, 20th ed. Lippincott Williams & Wilkins: Philadelphia, Pa., 2000 and Sheth et al. Compressed Tablets, in Pharmaceutical Dosage Forms: Tablets, Vol 1. edited by H. A. Lieberman and L. Lachman, Dekker N.Y. (1980).

A modified release layer or layers of a tablet of the present invention can be prepared by incorporating release retarding excipients into the above-described formulation for the quick release API containing layer, and either completely omitting or reducing the amount of disintegrants.

Examples of release retarding excipients include, but are not limited to hydrophilic polymers such as hydroxypropylmethylcellulose, hydroxymethylcellulose, hydroxypropylcellulose and hydroxyethylcellulose, and which swell in contact with aqueous liquids, and control release of the API by diffusion through the swollen polymer network.

Examples of other release retarding excipients include, but not limited to, waxes such as carnauba wax, bees wax stearic acid and gums such as acacia, acrylic polymers, shellac, zein, polyvinylpyrrolidine including crosslinked polyvinylpyrrolidinone, vinyl acetate copolymers, polyethylene oxides, polyvinyl alcohols, and combinations comprising at least one of the foregoing materials.

The modified release layer or layers of the tablets are formulated, for example, by preparing the powder mixture of API or APIs with release retarding excipients by dry blending or granulating or slugging, adding a lubricant and pressing the mixture into tablet layer.

The inert layer or layers may comprise any biocompatible compound or mixture of compounds. The inert layer may be soluble or insoluble, permeable or impermeable, pH dependent or pH independent or any combination thereof depending upon the API or APIs to be orally administered and/or the release mechanism required. Preferably, the inert layers are inert, insoluble and impermeable to API in the API containing layer. The inert layer comprises no API or API in an amount which does not significantly modify bioequivalence.

Examples of biocompatible materials for use in the inert layer include, but not limited to, waxes, polymers, gums and other pharmaceutically acceptable excipients either alone or in combination.

Examples of wax excipients include, but are not limited to, wax and wax-like excipients such as carnauba wax, vegetable wax, fruit wax, microcrystalline wax, bees wax (white or bleached, and yellow), hydrocarbon wax, paraffin wax, cetyl esters wax or a combination comprising at least one of the foregoing waxes. Other suitable wax excipients include, for example, fatty alcohols (such as lauryl, myristyl, stearyl, cetyl or specifically cetostearyl alcohol), hydrogenated vegetable oil, hydrogenated castor oil, fatty acids such as stearic acid, fatty acid esters including fatty acid glycerides (mono-, di-, and tri-glycerides), polyethylene glycol (PEG) having a molecular weight of greater than about 3000 number average molecular weight, $M_n$ (e.g. PEG 3350, PEG 4000, PEG 4600, PEG 6000, and PEG 8000), or a combination comprising at least one of the foregoing.

Examples of polymer excipients include, for example acrylic polymers, alkylcelluloses including substituted alkylcelluloses, shellac, zein, polyvinylpyrrolidine including crosslinked polyvinylpyrrolidinone, vinyl acetate copolymers, polyethylene oxides, polyvinyl alcohols, and combinations comprising at least one of the foregoing materials.

Suitable acrylic polymers that can be used in the inert layer include, but are not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly (methyl methacrylate) copolymer, polyacrylamide, aminoalkyl methacrylate copolymer, glycidyl methacrylate copolymers, or a combination comprising at least one of the foregoing polymers.

Suitable alkylcelluloses and substituted alkyl celluloses include, but are not limited to, methyl cellulose, ethylcellulose, hydroxy or carboxy substituted alkyl celluloses (e.g., hydroxyl propylcellulose, crosslinked hydroxypropylcellulose, carboxymethylcellulose, crosslinked sodium carboxymethylcellulose), hydroxy substituted alkyl-alkyl celluloses (e.g., hydroxypropylmethylcellulose), or a combination comprising at least one of the foregoing.

Examples of additional pharmaceutically acceptable excipients for use in the inert layer include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g.

acacia, sodium alginate, extract of Irish moss, panwar gum, ghatti gum, mucilage of isapol husks, carboxymethylcellulose, magnesium aluminum silicate (Veegum), and larch arabogalactan); alginates; polyethylene oxide; inorganic calcium salts; silicic acid; and combinations thereof.

Fillers, tablet binders and lubricants, including the aforementioned, can be used in the inert layer singly or in combination.

The inert layer of the tablet of the present invention is formulated, for example, by preparing a powder mixture by dry blending or granulating or slugging, adding a lubricant and pressing into a tablet layer or layers.

One or more of the quick release layers, one or more of the inert layers and one or more of the modified release layers are then compressed together to form a single core tablet for the multilayer tablet of the present invention.

The core tablet is then coated with the functional coating or film. By "functional coating or film" it is meant a coating that modifies the release properties of the formulation. Examples of such coatings or films include, but are not limited to, controlled release, delayed release, modified release, pH dependent, pH independent coatings, and any combinations thereof.

The functional coating material can be in the form of a film coating comprising a solution or dispersion or a compressible powder mixture of a hydrophilic or hydrophobic polymer. Solvents used for application of the functional coating include pharmaceutically acceptable solvents, such as water, methanol, ethanol, methylene chloride, and a combination comprising at least one of the foregoing solvents.

Examples of functional coating materials include, but are not limited to, film forming polymers such as an alkylcellulose including methylcellulose or ethylcellulose, a hydroxyalkylcellulose such as hydroxymethylcellulose, hydroxyethylcellulose, hydroxypropylcellulose and hydroxybutylcellulose, a hydroxyalkyl alkylcellulose such as hydroxyethyl methylcellulose and hydroxypropyl methylcellulose, a carboxyalkylcellulose such as carboxymethylcellulose, an alkali metal salt of carboxyalkylcelluloses such as sodium carboxymethylcellulose, a carboxyalkyl alkylcellulose such as carboxymethyl ethylcellulose, a carboxyalkylcellulose ester, a starch, a pectin such as sodium carboxymethylamylopectine, a chitin derivate such as chitosan, a polysaccharide such as alginic acid, alkali metal and ammonium salts thereof, a carrageenan, a galactomannan, traganth, agar-agar, gum arabicum, guar gum and xanthan gum, acrylic acid, polyacrylic acid and the salts thereof, a polyvinylalcohol, a polyvinylpyrrolidone, a copolymer of polyvinylpyrrolidone with vinyl acetate, a polyalkylene oxide such as polyethylene oxide and polypropylene oxide and a copolymer of ethylene oxide and propylene oxide, or a combination comprising at least one of the foregoing.

The functional coating may optionally comprise a plasticizer, an additional film-former, a pore former, or a combination comprising at least one of the foregoing.

Examples of enteric polymers include, but are not limited to, polymers such as methacrylic acid-ethyl acrylate copolymer (1:1), ethacrylic acid-methyl methacrylate copolymer (1:1), methacrylic acid-methyl methacrylate copolymer (1:2), polyvinyl acetate phthalate (PVAP), hydroxypropyl methylcellulose acetate succinate (HPMCAS) and cellulose acetate phthalate (CAP). Additionally, dyestuffs or pigments can be added to the enteric polymer coating for product identification or to characterize the quantity of active compound, i.e., dosage. Further, the enteric polymer can be optionally modified to include a pore-forming agent thereby resulting in a semi-enteric coating.

The pore-forming agents used are preferably water soluble materials. Examples of pore-forming materials include, but are not limited to, polymers like hydroxyalkyl celluloses such as hydroxymethyl cellulose, hydroxyethyl cellulose, hydroxypropyl cellulose and hydroxybutylcellulose, hydroxyalkyl alkylcelluloses such as hydroxyethyl methylcellulose and hydroxypropyl methylcellulose, polyvinylalcohols, polyvinylpyrrolidones, copolymers of polyvinylpyrrolidone with vinyl acetate, sugars, salts and combinations thereof.

In some embodiments, prior to applying the functional coating or film, the core tablet is coated with a subcoating or non-functional coating and then coated with the functional coating or film to avoid interactions of the API with the functional coating or film. By "non-functional coating" it is meant a coating that does not significantly modify the release properties of the total formulation, for example, a cosmetic coating or an interlayer coating used to separate a functional coating from other components of the formulation. Examples of subcoating materials include, but are not limited to, film forming polymers like hydroxyalkyl celluloses such as hydroxymethyl cellulose, hydroxyethyl cellulose, hydroxypropyl cellulose and hydroxybutylcellulose, hydroxyalkyl alkylcelluloses such as hydroxyethyl methylcellulose and hydroxypropyl methylcellulose, polyvinylalcohols, polyvinylpyrrolidones, copolymers of polyvinylpyrrolidone with vinyl acetate, and combinations thereof.

Any orally active agent can be included as an API in the API containing layers of the tablets of the present invention. Examples of APIs include, but are not limited to, alpha-2 adrenergic agents, analgesics, angiotensin-converting enzyme (ACE) inhibitors, antianxiety agents, antiarrhythmics, antibacterials, antibiotics, anticoagulants, anticonvulsants, antidepressants, antidiabetics, antiemetics, antiepileptics, antifungals, antihelminthics, antihistamines, antihyperlipidemics, antihypertensives, antiinfectives, antimalarials, antimicrobials, antimigraine agents, antimuscarinic agents, antineoplastic agents, antiprotozoals, antipsychotics, antispasmodics, antiretroviral agents, antivirals, attention-deficit hyperactivity disorder (ADHD) agents, β-blockers, calcium channel blockers, chemotherapeutic agents, cholinesterase inhibitors, Cox-2 inhibitors, decongestants, diuretics, histamine-2 receptor antagonists, hypnotics, hypoglycemic agents, hypotensive agents, immunosuppressants, lipotropics, neuroleptics, opioid analgesics, peripheral vasodilators/vasoconstrictors, proton pump inhibitors, sedatives, serotonin receptor agonists, sympathomimetics as well as pharmaceutically acceptable salts, solvates, hydrates, stereoisomers (racemates, individual enantiomers or diastereomers, or any combination thereof), or polymorphs thereof, or pharmaceutically acceptable combinations comprising at least one of the foregoing active agents, and the like.

While any API administered orally can be formulated in accordance with the present invention, these functionally coated multilayer tablets provide a particularly useful formulation to achieve customized levels of controlled release of specific APIs and can achieve simultaneous release of two or more different APIs and different release rates from a single tablet.

The API may be the same in each API containing layer of the present invention or it may be different.

When the tablet is administered, the API from the quick release layer, if present, is released relatively faster regardless of the functional coating being present and the API release from the modified release layer is controlled by both the matrix and functional coat. The inert layer prevents the effect of one API containing layer on the other.

Advantages of the tablets of the present invention include, but are not limited to, reduced food effect as well as enhanced reproducibility due to the fact that the dosage form is intact throughout the GI tract while providing for a tablet which can release multiple APIs at different rates and/or which provides for bi-phasic API release. The functionally coated multilayer tablets of the present invention are also much easier to manufacturer and provide a safer more reliable means for administration of APIs than coated tablets requiring laser driven ports or holes in the coating for API release.

The following nonlimiting examples are provided to further illustrate the present invention.

EXAMPLES

Example 1: Preparation of Quick Release Pioglitazone HCl (30 mg) and Extended Release Metformin HCl (1000 mg) Multilayer Tablets The quick release drug containing layer contained Pioglitazone HCl (30.00 mg), microcrystalline cellulose (50.00 mg), lactose monohydrate (78.00 mg), hydroxypropyl Cellulose (30.00 mg), Croscarmellose sodium (10.00 mg) and magnesium stearate (2.00 mg).

The extended release drug containing layer contained Metformin HCl (1000.00 mg), carnauba wax (290.00 mg), stearic acid (190.00 mg), silicon dioxide (10.00 mg) and magnesium stearate (10.00 mg).

The inert layer contained carnauba wax (100.00 mg), dibasic calcium phosphate (58.00 mg), stearic acid (40 mg) and magnesium stearate (2.00 mg).

The subcoating contained hydroxypropyl methyl cellulose (45.00 mg/tablet), polyethylene glycol 400 (12.00 mg/tablet) and purified water which was removed during processing.

The extended release coating contained Surelease (98.00 mg/tablet), hydroxypropyl methyl cellulose (98.00 mg/tablet) and purified water which was removed during processing.

The quick release drug containing layer of the core tablet was prepared as follows:

Pioglitazone HCl was dry blended with all the ingredients except Croscarmellose sodium and magnesium stearate and granulated with purified water. The granulate was dried and milled through a suitable screen. Croscarmellose sodium and Magnesium stearate were screened and then added to the milled granules. The mixture was then blended for about 2 minutes.

The extended release drug containing layer of the core tablet was prepared as follows:

Metformin HCl and Carnauba wax were mixed and granulated with a solution of stearic acid in ethyl alcohol. The granulate was then dried, milled through a suitable screen. Silicon dioxide and Magnesium stearate were screened and then added to the milled granules. The mixture was then blended for another 2 minutes.

The inert layer was prepared as follows: Carnauba wax and dicalcium phosphate were mixed and granulated with a solution of stearic acid in ethyl alcohol. The granulate was then dried, milled through a suitable screen. Magnesium stearate was screened and then added to the milled granules. The mixture was then blended for another 2 minutes.

The blends were then compressed into a multi-layer core tablet in the following sequence: extended release drug containing layer, inert layer and quick release drug containing layer using a multi-layer tablet press. Core tablets were then subcoated.

The subcoating was prepared by dissolving hydroxypropyl methyl cellulose and polyethylene glycol 400 in purified water and sprayed as a coating solution onto the multi-layer core tablet in a coating pan.

The extended release coating was prepared as follows: In a container purified water was mixed with hydroxypropyl methyl cellulose using mixer until the hydroxypropyl methyl cellulose was completely dissolved. The hydroxypropyl methyl cellulose solution was then added to the Surelease dispersion and mixed for 15 minutes. The resulting dispersion was mixed during the entire coating process. Using the coating pan, the Surelease/hydroxypropyl methyl cellulose dispersion was sprayed onto the subcoated tablets until the required weight gain was achieved.

Example 2: Preparation of Extended Release Multilayer Tablets of Paroxetine HCl with Loading Dose The quick release drug containing layer contained Paroxetine HCl (5.00 mg), microcrystalline cellulose (30.00 mg), lactose monohydrate (49.00 mg), hydroxypropyl Cellulose (10.00 mg), Croscarmellose sodium (5.00 mg) and magnesium stearate (1.00 mg).

The Extended release drug containing layer contained Paroxetine HCl (20.00 mg), carnauba wax (46.00 mg), stearic acid (20.00 mg), hydroxypropyl Cellulose (10.00 mg), silicon dioxide (3.00 mg) and magnesium stearate (1.00 mg).

The inert layer contained carnauba wax (59.00 mg), dibasic calcium phosphate (39.00 mg), stearic acid (10.00 mg) and magnesium stearate (1.00 mg).

The subcoating contained hydroxypropyl methyl cellulose (8.00 mg/tablet), polyethylene glycol 400 (1.00 mg/tablet) and purified water which was removed during processing.

The extended release coating contained Surelease (7.50 mg/tablet), hydroxypropyl methyl cellulose (7.50 mg/tablet) and purified water which was removed during processing.

The quick release drug containing layer of the core tablet was prepared as follows:

Paroxetine HCl was dry blended with all the ingredients except Croscarmellose sodium and magnesium stearate and granulated with purified water. The granulate was dried and milled through a suitable screen. Croscarmellose sodium and Magnesium stearate were screened and then added to the milled granules. The mixture was then blended for about 2 minutes.

The extended release drug containing layer of the core tablet was prepared as follows:

Paroxetine HCl and Carnauba wax were mixed and granulated with a solution of stearic acid in ethyl alcohol. The granulate was then dried, milled through a suitable screen. Hydroxypropyl cellulose, Silicon dioxide and Magnesium stearate were screened and then added to the milled granules. The mixture was then blended for another 2 minutes.

The inert layer was prepared as follows: Carnauba wax and dicalcium phosphate were mixed and granulated with a solution of stearic acid in ethyl alcohol. The granulate was then dried, milled through a suitable screen. Magnesium stearate was screened and then added to the milled granules. The mixture was then blended for another 2 minutes.

The blends were then compressed into a multi-layer core tablet in the following sequence: extended release drug containing layer, inert layer and quick release drug containing layer using a multi-layer tablet press. Core tablets were then subcoated.

The subcoating was prepared by dissolving hydroxypropyl methyl cellulose and polyethylene glycol 400 in purified water and sprayed as a coating solution onto the multi-layer core tablet in a coating pan.

The extended release coating was prepared as follows: In a container purified water was mixed with hydroxypropyl methyl cellulose using mixer until the hydroxypropyl methyl cellulose was completely dissolved. The hydroxypropyl methyl cellulose solution was then added to the Surelease dispersion and mixed for 15 minutes. The resulting dispersion was mixed during the entire coating process. Using the coating pan, the Surelease/hydroxypropyl methyl cellulose dispersion was sprayed onto the subcoated tablets until the required weight gain was achieved.

Example 3: Preparation of Quick Release Phenylephrine HCl (7.5 mg) and Extended Release Phenylephrine HCl (22.5 mg) Multilayer Tablets The quick release drug containing layer contained Phenylephrine HCl (7.50 mg), microcrystalline cellulose (31.50 mg), lactose monohydrate (45.00 mg), hydroxypropyl Cellulose (10.00 mg), Croscarmellose sodium (5.00 mg) and magnesium stearate (1.00 mg).

The Extended release drug containing layer contained Phenylephrine HCl (22.50 mg), carnauba wax (120.00 mg), stearic acid (30.00 mg), hydroxypropyl Cellulose (20.00 mg), silicon dioxide (5.00 mg) and magnesium stearate (2.50 mg).

The inert layer contained carnauba wax (55.00 mg), dibasic calcium phosphate (24.00 mg), stearic acid (20 mg) and magnesium stearate (1.00 mg).

The subcoating contained hydroxypropyl methyl cellulose (14.00 mg/tablet), polyethylene glycol 400 (2.00 mg/tablet) and purified water which was removed during processing.

The extended release coating contained Surelease (20.00 mg/tablet), hydroxypropyl methyl cellulose (20.00 mg/tablet) and purified water which was removed during processing.

The quick release drug containing layer of the core tablet was prepared as follows:

Phenylephrine HCl were dry blended with all the ingredients except Croscarmellose sodium and magnesium stearate and granulated with purified water. The granulate was dried and milled through a suitable screen. Croscarmellose sodium and Magnesium stearate were screened and then added to the milled granules. The mixture was then blended for about 2 minutes.

The extended release drug containing layer of the core tablet was prepared as follows:

Phenylephrine HCl and Carnauba wax were mixed and granulated with a solution of stearic acid in ethyl alcohol. The granulate was then dried, milled through a suitable screen. Silicon dioxide and Magnesium stearate were screened and then added to the milled granules. The mixture was then blended for another 2 minutes.

The inert layer was prepared as follows: Carnauba wax and dicalcium phosphate were mixed and granulated with a solution of stearic acid in ethyl alcohol. The granulate was then dried, milled through a suitable screen. Magnesium stearate was screened and then added to the milled granules. The mixture was then blended for another 2 minutes.

The blends were then compressed into a multi-layer core tablet in the following sequence: extended release drug containing layer, inert layer and quick release drug containing layer using a multi-layer tablet press. Core tablets were then subcoated.

The subcoating was prepared by dissolving hydroxypropyl methyl cellulose and polyethylene glycol 400 in purified water and sprayed as a coating solution onto the multi-layer core tablet in a coating pan.

The extended release coating was prepared as follows: In a container purified water was mixed with hydroxypropyl methyl cellulose using mixer until the hydroxypropyl methyl cellulose was completely dissolved. The hydroxypropyl methyl cellulose solution was then added to the Surelease dispersion and mixed for 15 minutes. The resulting dispersion was mixed during the entire coating process. Using the coating pan, the Surelease/hydroxypropyl methyl cellulose dispersion was sprayed onto the subcoated tablets until the required weight gain was achieved.

Example 4: Preparation of Quick Release Cetirizine HCl (5 mg) and Extended Release with Loading Dose of Phenylephrine HCl (30 mg) Multilayer Tablets The quick release drug containing layer contained Cetirizine HCl (5.00 mg), Phenylephrine HCl (7.50 mg), microcrystalline cellulose (31.50 mg), lactose monohydrate (40.00 mg), hydroxypropyl Cellulose (10.00 mg), Croscarmellose sodium (5.00 mg) and magnesium stearate (1.00 mg).

The Extended release drug containing layer contained Phenylephrine HCl (22.50 mg), carnauba wax (120.00 mg), stearic acid (30.00 mg), hydroxypropyl Cellulose (20.00 mg), silicon dioxide (5.00 mg) and magnesium stearate (2.50 mg).

The inert layer contained carnauba wax (55.00 mg), dibasic calcium phosphate (24.00 mg), stearic acid (20 mg) and magnesium stearate (1.00 mg).

The subcoating contained hydroxypropyl methyl cellulose (14.00 mg/tablet), polyethylene glycol 400 (2.00 mg/tablet) and purified water which was removed during processing.

The extended release coating contained Surelease (20.00 mg/tablet), hydroxypropyl methyl cellulose (20.00 mg/tablet) and purified water which was removed during processing.

The quick release drug containing layer of the core tablet was prepared as follows:

Cetirizine HCl and Phenylephrine HCl were dry blended with all the ingredients except Croscarmellose sodium and magnesium stearate and granulated with purified water. The granulate was dried and milled through a suitable screen. Croscarmellose sodium and Magnesium stearate were screened and then added to the milled granules. The mixture was then blended for about 2 minutes.

The extended release drug containing layer of the core tablet was prepared as follows:

Phenylephrine HCl and Carnauba wax were mixed and granulated with a solution of stearic acid in ethyl alcohol. The granulate was then dried, milled through a suitable screen. Silicon dioxide and Magnesium stearate were screened and then added to the milled granules. The mixture was then blended for another 2 minutes.

The inert layer was prepared as follows: Carnauba wax and dicalcium phosphate were mixed and granulated with a solution of stearic acid in ethyl alcohol. The granulate was then dried, milled through a suitable screen. Magnesium stearate was screened and then added to the milled granules. The mixture was then blended for another 2 minutes.

The blends were then compressed into a multi-layer core tablet in the following sequence: extended release drug containing layer, inert layer and quick release drug containing layer using a multi-layer tablet press. Core tablets were then subcoated.

The subcoating was prepared by dissolving hydroxypropyl methyl cellulose and polyethylene glycol 400 in purified water and sprayed as a coating solution onto the multi-layer core tablet in a coating pan.

The extended release coating was prepared as follows: In a container purified water was mixed with hydroxypropyl methyl cellulose using mixer until the hydroxypropyl methyl cellulose was completely dissolved. The hydroxypropyl methyl cellulose solution was then added to the Surelease dispersion and mixed for 15 minutes. The resulting dispersion was mixed during the entire coating process. Using the coating pan, the Surelease/hydroxypropyl methyl cellulose dispersion was sprayed onto the subcoated tablets until the required weight gain was achieved.

What is claimed is:

1. A functionally coated multilayer tablet for oral administration comprising:
   (a) a core tablet comprising
      (i) a quick release layer or layers comprising one or more active pharmaceutical ingredients (APIs);
      (ii) a modified release layer or layers comprising one or more APIs and a release retarding excipient; and
      (iii) an inert layer separating said quick release layer or layers and said modified release layer or layers, wherein said inert layer is insoluble and impermeable;
   (b) a functional coating or film surrounding the core tablet, wherein said coating or film comprises a pore-forming agent which permits quick release of the API from the quick release layer regardless of the functional coating or film being present while providing release of the API from the modified release layer controlled by the release retarding excipient, inert layer and functional coating or film.

2. The functionally coated multilayer tablet of claim 1 further comprising a subcoating between said core tablet and said functional coating.

3. The functionally coated multilayer tablet of claim 1 wherein the one or more APIs of the quick release layer or layers and the one or more APIs of the modified release layer or layers are the same.

4. The functionally coated multilayer tablet of claim 1 wherein the one or more APIs of the quick release layer or layers and the one or more APIs of the modified release layer or layers are different.

5. The functionally coated multilayer tablet of claim 1 further comprising an additional functional coating or film.

6. A method for formulating the multilayer tablet of claim 1 comprising:
   (a) preparing a quick release API containing tablet layer or layers and a modified release API containing tablet layer or layers, said modified release layer or layers comprising one or more APIs and a release retarding excipient;
   (b) preparing an inert layer which is insoluble and impermeable and compressing together the quick release layer or layers, the inert layer or layers, and the modified release layer or layers into a core tablet so that the inert layer or layers separates the quick release layer or layers and the modified release layer or layers; and
   (c) coating the core tablet with a functional coating or film comprising a pore-forming agent which permits quick release of the API from the quick release layer or layers regardless of the functional coating or film being present while providing release of the API from the modified release layer or layers controlled by the release retarding excipient, inert layer and functional coating or film.

7. The method of claim 6 further comprising applying a subcoating to the core tablet prior to coating the core tablet with the functional coating or film.

* * * * *